United States Patent [19]
Ishida

[11] Patent Number: 5,973,144
[45] Date of Patent: Oct. 26, 1999

[54] HIGH CHAR YIELD BENZOXAZINES

[76] Inventor: Hatsuo Ishida, 2903 Weybridge Rd., Shaker Heights, Ohio 44120

[21] Appl. No.: 08/943,989

[22] Filed: Oct. 3, 1997

[51] Int. Cl.$^6$ .................................................. C07D 265/16
[52] U.S. Cl. .............................. 544/73; 544/63; 544/69; 544/74; 544/90; 544/105
[58] Field of Search ................................ 544/69, 73, 90, 544/63, 74, 105

[56] References Cited

U.S. PATENT DOCUMENTS 5,543,516  8/1996  Ishada ....................................... 544/69

Primary Examiner—Richard L. Raymond
Attorney, Agent, or Firm—Hudak & Shunk Co., L.P.A.

[57] ABSTRACT

Benzoxazine monomers, oligomers and polymers are desirably modified by adding pendant functional groups to either the amine or phenolic reactants. These pendant functional groups can be activated at temperatures generally from about 25° C. to about 300° C. to form chemical bonds between said benzoxazine monomers, oligomers and polymers. The additional chemical bonds increase the thermal stability of benzoxazine polymers such that they can withstand higher use temperature, act as more effective flame barriers, or result in higher amounts of char if used as a precursor to high temperature (600–1000° C. reaction condition) chars.

7 Claims, No Drawings

HIGH CHAR YIELD BENZOXAZINES

FIELD OF INVENTION

This invention relates to benzoxazines made by reacting phenolic compounds, aldehydes, and amines wherein the phenolic compounds and/or the amines have a second reactive functional group. The second reactive functional group provides an additional pathway (other than forming benzoxazine rings) to increase molecular weight such as by crosslinking and/or branching etc. Improved physical properties such as increased modulus and percent char derived from polymerized benzoxazines are observed.

BACKGROUND OF THE INVENTION

Polymers derived from the ring opening polymerizations of benzoxazine compounds compete with phenolic, epoxy, and other resins in various applications. Benzoxazines have advantages over conventional phenolic resins as the benzoxazine can be readily molded from the melt and then polymerized by simply heating it without releasing reaction by-products.

Phenolic resins have been used for years in applications requiring low flammability and high char yields. These uses include aircraft interiors which often include a thin layer of flame inhibiting phenolics in the interior shell and in electronics such as circuit boards, connectors, etc. A drawback of many phenolics are volatiles which may be produced during crosslinking (said volatiles often producing undesirable voids in the finished article) and residual catalyst and other reactants retained in the resins (which impart undesirable color or undesirable properties on aging. Benzoxazines avoid these problems (volatiles and residuals) due to polymerizing by a method not producing volatiles (supposedly ionic ring opening polymerizations) and not requiring catalysts. Having lower viscosities, the benzoxazines are easier to mold than phenolics.

Another use for benzoxazine polymers is as a precursor for chars produced between 400 and 800° C. In this application they compete with coal tar pitch and phenolic resins which can produce between 30 and 65 weight % char upon exposure to elevated temperatures. These chars are useful as components in aircraft brakes and as thermal insulators or barriers.

As the char yield of polymers from benzoxazines are in the same ranges as coal tar pitch and phenolic resins there has been little motivation (other than processability and properties for non-char forming applications) to use benzoxazines.

SUMMARY OF INVENTION

The addition of functional groups other than benzoxazine to benzoxazine compounds can increase physical properties such as the char yield of polymers derived from the polymerization of benzoxazines. The desired functional groups are those capable of forming chemical crosslinks which are moderately or fully stable to high temperature charring, used to form carbon rich composites. The desired functional groups can be an integral part of the amine compound or the phenolic compound or both. Generally the most thermally stable crosslinks (linkages) include imides, six membered rings, other cyclic structures and double bonds derived from acetylene or nitrile. The percent char tests in the examples reveal the additional functional groups can significantly increase the char yield over nearly identical polymers not having the functional groups. Possible mechanisms for increasing percentage yield during charring include a) preparing higher molecular weight polymer, b) forming more temperature stable intermediates, and c) preventing the volatilization of polymer fragments by increasing their molecular weight or binding them to other polymers.

DETAILED DESCRIPTION

Benzoxazines are prepared by reacting a phenolic compound with an aldehyde and an amine desirably aromatic. U.S. Pat. No. 5,543,516, hereby incorporated by reference, sets forth a generally solventless method of forming benzoxazines. Optionally, solvents can be used to prepare benzoxazines. The reaction time can vary widely with reactant concentration, reactivity and temperature. Times desirably vary from a few minutes for solventless to a few hours, e.g. 6 or 10 for diluted reactants. If a water based solution of formaldehyde is used as one reactant then a water miscible organic solvent is sometimes desirable. If one or more reactant is a liquid it may be used to dissolve the other components. If all of the components are solids they may be premixed as solids and then melted or first melted and then mixed. The temperature of reaction can be determined by routine experimentation noting the formation of benzoxazine and less desired products and optimizing temperature and time for a desirable product. Desirable temperatures are from about 0° C. to about 250° C., and preferably from about 0 or 50° C. to about 150° C.

The reaction synthesis may be conducted at atmospheric pressure or at a pressure up to about 100 psi. In some instances, a reaction carried out under pressure constitutes a preferred mode since fewer byproducts are produced. When a polyfunctional benzoxazine is being prepared, higher pressures generally results in relatively higher amounts of difunctional benzoxazine monomers.

The relative amounts of reactants required will depend upon their chemical nature, e.g., the number of reactive groups taking part in the reaction. The stoichiometry is well within the skills of those conversant with the art, and the required relative amounts of reactants are readily selected depending upon the functionality of the reacting compounds.

In addition to the methods for carrying out the single step reaction noted above, the reaction may also be carried out by using continuous processing machinery, for instance, screw extruders and static mixers. It is thus possible to feed the unreacted components into the feed end of an extruder while maintaining the extruder at the desired reaction temperature. The extruder is operated at an RPM sufficient to provide the residence time required to carry out the chemical reaction within the extruder, and the finished benzoxazine product is automatically extruded at the conclusion of the reaction period.

The ultimate reaction mixture contains the desired benzoxazine monomer and oligomers thereof, as well as impurities. If desired, the mixture may be purified to obtain a more concentrated form of the product described, for example by well-known crystallization or solvent washing techniques. The resulting product can be partially or fully shaped by melt processing in conventional polymer and/or composite processing equipment. It can be polymerized by heating the monomer, for instance, to from about 120 to 260° C.

The polymerization of benzoxazines is believed to be an ionic ring opening polymerization which converts the oxazine ring to another structure, e.g. linear polymer or larger heterocyclic rings. It is thought that a chain transfer"

step(s) limits the molecular weight of the resulting polymer and causes some branching. FTIR (Fourier transform infrared) analysis is often used to monitor the conversion of the oxazine rings to polymers to provide an estimate of the rate of polymerization at different temperatures. NMR (nuclear magnetic resonance) spectroscopy can also be used to monitor conversion of benzoxazine monomers to polymer. Many NMR techniques require the sample to be put into solution while FTIR can also monitor the change in the amount of other reactive functional groups such as the acetylene groups in the examples in solution, melt, or solid films.

The polymer from the polymerization of the benzoxazine monomers can be partially or fully converted to a high carbon char by heating in an atmosphere of air, nitrogen or other gas to a temperature from about 400° C. to about 700, 800 or 1000° C. The yield of char on heating to 800° C. in nitrogen is desirably at least 65, 70 or 72 wt. % of the initial sample weight, more desirably at least 75 wt. %, and preferably from about 80 or 85 to about 92 wt. % of the original sample weight.

One or more precursors to the benzoxazines in this application are functionalized with additional functional groups to increase thermal stability and char yields. Examples of similar functional groups and their chemistry to increase performance of thermoset polymers has been set forth in "High Performance Thermosets, Chemistry, Properties, and Application" by Shiow-Ching Lin and Eli M. Pearce published by Hanser Publishers Munich, 1994. Those examples can supplement this application with more specific reaction conditions.

The aldehyde reactants include vaporous formaldehyde; paraformaldehyde; polyoxymethylene; as well as aldehydes having the general formula RCHO, where R is aliphatic, including mixtures of such aldehydes, desirably having from 1 to 12 carbon atoms.

The conventional phenolic reactants for benzoxazines include, for instance, compounds having one or more phenolic groups of the formula

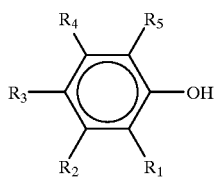

in which $R_1$ through $R_5$ can independently be H; OH; aliphatics from 1 to 10 carbon atoms, linear or branched; aromatics having from 6 to 12 carbon atoms, combinations of aliphatics and aromatics having from 7 to 12 carbon atoms; phosphines having up to 6 carbon atoms; amines having up to 6 carbon atoms or halogens; in which at least one of the ortho positions to the OH is unsubstituted and in polyphenolic compounds an oxygen, methylene, etc. Further nonhydrogen and nonhalogen $R_1$ through $R_5$ groups as described above less one or more H or P=O can serve to connect two or more phenolic groups creating a polyphenolic compound which can be the phenolic compound. Example or mono-functional phenols include phenol; cresol; 2-bromo-4-methylphenol; 2-allyphenol; 1,4-aminophenol; and the like. Examples of difunctional phenols (polyphenolic compounds) include phenolphthalane; biphenol; 4-4'-methylene-di-phenol; 4-4'-dihydroxybenzophenone; bisphenol-A; 1,8-dihydroxyanthraquinone; 1,6-dihydroxnaphthalene; 2,2'-dihydroxyazobenzene; resorcinol; fluorene bisphenol; and the like. Examples of trifunctional phenols comprise 1,3,5-trihydroxy benzene and the like. Polyvinyl phenol is also a suitable component for the benzoxazine compounds that constitute the subject of the invention.

Preferred phenolic compounds include

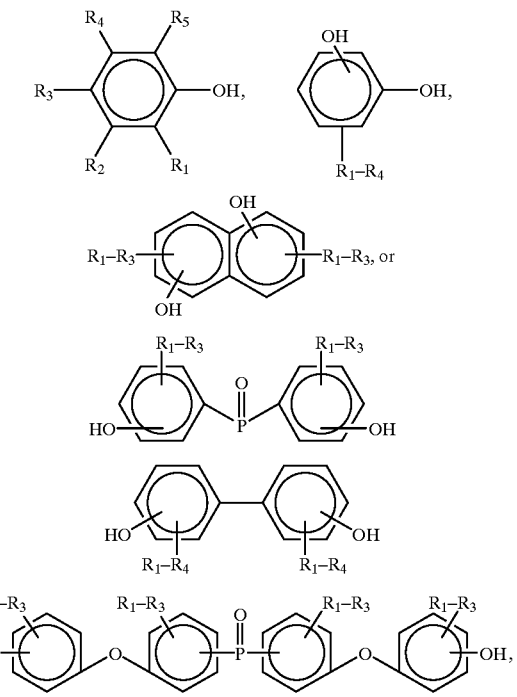

or combinations thereof,

If the phenolic compound or polyphenolic compound is to carry an added functional group then $R_1$–$R_5$ can further be selected from the following functional groups or combinations of $R_1$–$R_5$ and said functional groups as long as at least one $R_1$–$R_5$ group adjacent to the hydroxyl of the phenol is a hydrogen for the hydroxyl groups that are to form benzoxazine rings.

Examples of these functional groups include

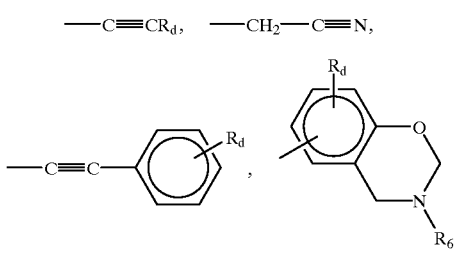

where $R_6$ is an alkyl of 1 to 8 carbon atoms or an aromatic group of 6 to 12 atoms or combinations thereof,

-continued

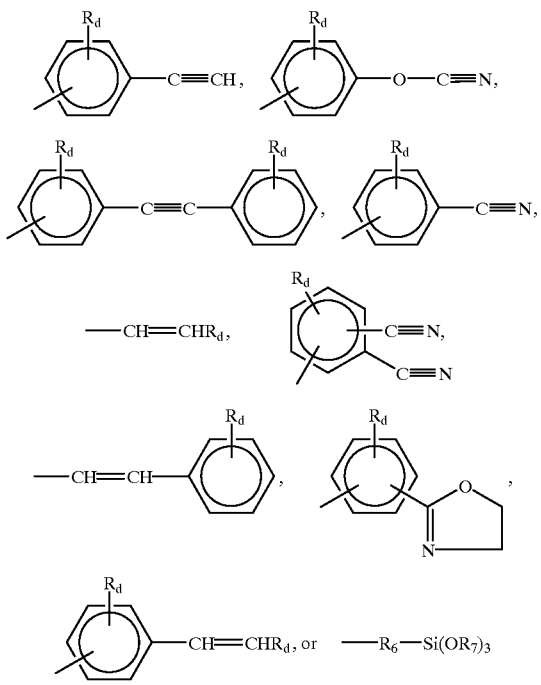

where $R_7$ is an alkyl of 1 to 5 carbon atoms, a halogen, a phenyl or combinations thereof so $OR_7$ is a hydrolyzable functional group such as $OCH_3$, $OC_2H_5$, $OC_3H_7$, OPh, OCl and so on.

or combinations of said functional groups, and wherein Rd is one or more H, halogen, alkyl of 1 to 6 carbon atoms, or aromatic or alkyl substituted aromatic or aromatic substituted alkyl of 6 to 12 carbon atoms and $R_6$ is as previously defined.

Alternatively the phenolic compound can include a first functional group which readily reacts with a second different functional group to form a chemical bond as described later for the amines.

Amine reactants for forming the benzoxazines include amines desirably having from 2 to 40 carbon atoms and optionally heteroatoms of O, N, S, and halogen and desirably include functional groups that can form chemical bonds under polymerization conditions similar to or different from those of polymerizing benzoxazines. Preferred functional groups include those containing one or more carbon to carbon triple bonds, carbon to carbon double bonds, and carbon to nitrogen triple bonds. Intermediate between the nitrogen of the amine and the functional group optionally can be an alkyl group of 1 to 6 carbon atoms or an aromatic group, alkylsubstituted aromatic or aromatic substituted alkyl of 6 to 12 carbon atoms.

Examples of these functional groups include

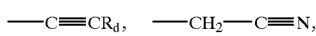

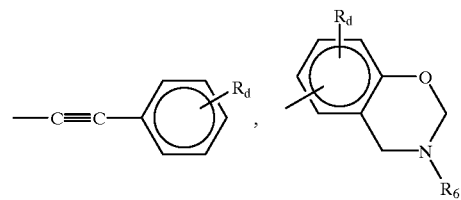

where $R_6$ is an alkyl of 1 to 8 carbon atoms or an aromatic group of 6 to 12 atoms or combinations thereof,

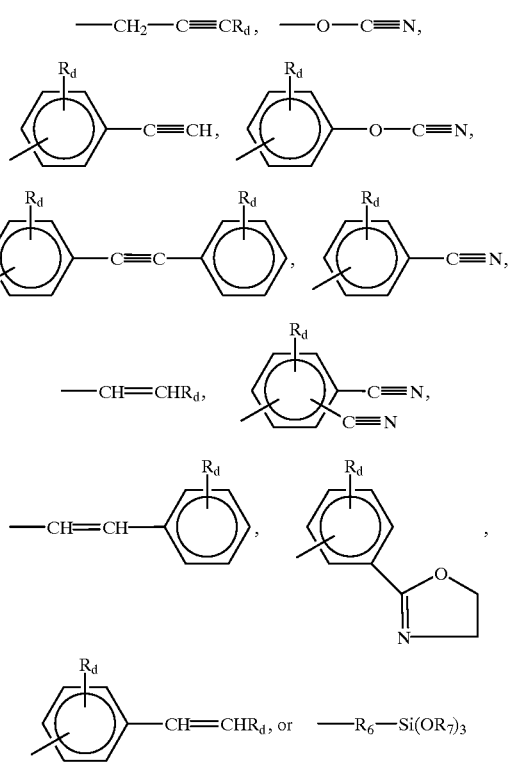

where $R_7$ is an alkyl of 1 to 5 carbon atoms, a halogen a phenyl or combinations thereof so $OR_7$ is a hydrolyzable functional group such as $OCH_3$, $OC_2H_5$, $OC_3H_7$, OPh, OCl and so on.

or combinations of said functional groups, wherein Rd is one or more H, halogen, alkyl of 1 to 6 carbon atoms, or aromatic or alkyl substituted aromatic or aromatic substituted alkyl of 6 to 12 carbon atoms and $R_6$ is as previously defined.

The above functional groups for amines are preferred as their double or triple bond in the additional functional groups can react with themselves to form a crosslink or chain extend the polymer. They do not need a second different functional group to form a chemical bond.

Another group of pendant functional groups (which can be pendant from the phenolic compound, polyphenolic compound, or amine compound or combinations thereof) are those wherein the first functional group readily reacts with one or more second different functional groups to form a chemical bond. These functional groups include the imide rings, O—O≡N,

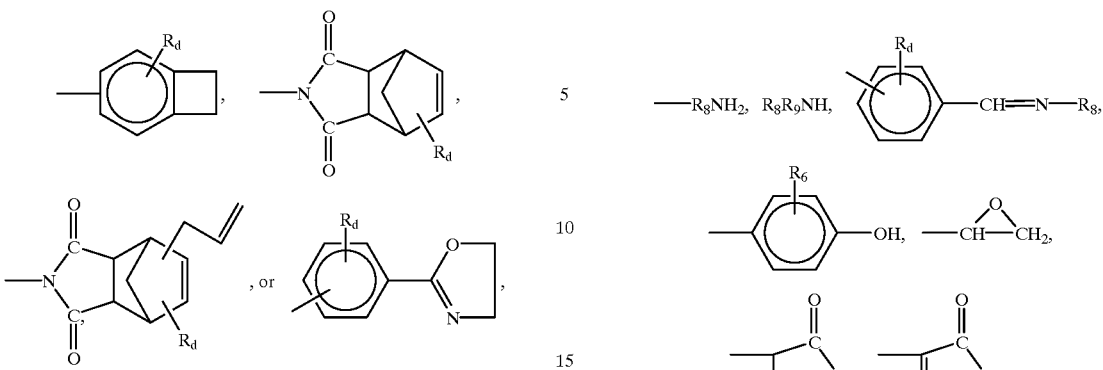

and amine groups wherein Rd is as previously defined. The first functional group(s) are set forth below in combination with the second functional group(s) with which they react. It is understood that with these functional groups there must be a combination of a first and second functional group in the final benzoxazine compound or in a blend of benzoxazine compounds. That is, a) at least one first pendant

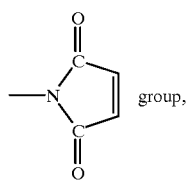

group, and at least one second pendant

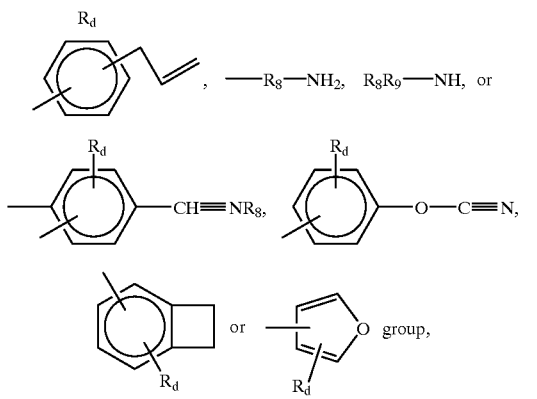

or combinations thereof
wherein $R_8$ and $R_9$ are independently selected from alkyl groups of 1 to 6 carbon atoms; aromatic, aromatic substituted allyl or alkyl substituted aromatic group of 6 to 12 carbon atoms or combinations thereof and $R_d$ is as defined above and $R_d$ is as previously defined, or b) at least one first pendant

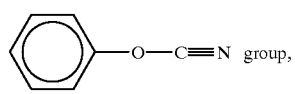 group, and at least one second pendant $-R_8NH_2$, $R_8R_9NH$,

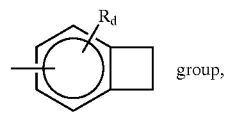

or combinations thereof wherein $R_8$ and $R_9$ are individually selected from alkyls of 1 to 6 carbon atoms, or aromatics or alkyl substituted aromatic or aromatic substituted alkyl groups of 6 to 12 carbon atoms or combinations thereof.

or c) at least one first pendant

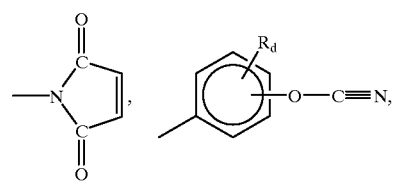

and at least one second pendant

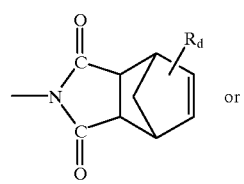

or $-C-C-R_d$ group, or combinations thereof or d) at least one first pendant

-continued

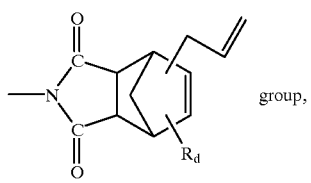 group, and a second pendant

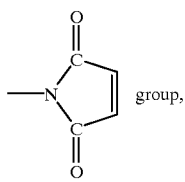 group, or e) at least one first pendant

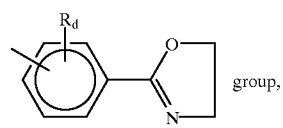 group, group and at least one second pendant

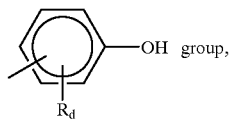 group, f) at least one first pendant SiH group, and at least one second pendant —CH=CH$_d$ group, or g) at least one first and at least one second

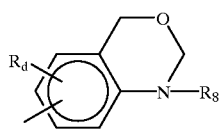

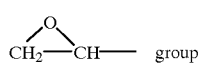 group wherein R$_d$ and R$_7$ are as previously defined.

The amine reactant requires a primary amine in order to obtain a benzoxazine ring structure. Besides the amines with functional group polymerizable by other than benzoxazine formation or ring opening groups thereon some non-functional group containing amines may be present. Such compounds include those having the general formula

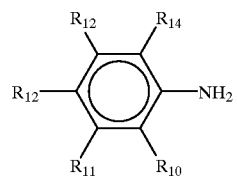

in which R$_{10}$ through R$_{14}$, independently, are H, aliphatic substituents having from 1 to 10 carbon atoms, and aromatic substituents having from 6 to 12 carbon atoms, and further in which said substituents may include an amine, and a halogen. The amine compound may either be amine terminated, or the amine may be present in the form of a side chain on the compound.

It is also understood that the phenolic compound can include the chemical formulas for the aromatic amine compound wherein a single or multiple hydroxyl groups are substituted for the NH$_2$ for example

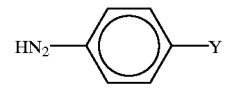

can be

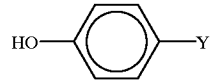

wherein Y is a functional group. Similarly the amine can be a formula where one or more NH$_2$ is substituted for a hydroxyl group so that

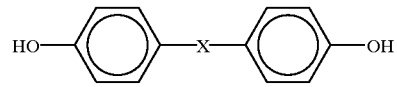

can teach

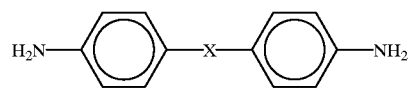

where X is an R$_1$–R$_5$ group.

Silicones such as polydimethyl siloxane, as well as copolymers thereof which contain a primary amine group can also be employed. Illustrative of useful silicone compounds, are amine-functional silicones having the general formula

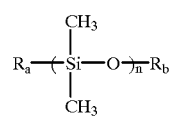

in which R$_a$ and R$_b$, independently, are hydrogen, a halogen, an aliphatic group of from 1 to 10 carbon atoms, or an aromatic group of from 6 to 12 carbon atoms, and in which at least one of R$_a$ and R$_b$ contains a primary amine group as a part thereof. Either monomeric or polymeric compounds having a primary amine included therein are satisfactory for producing the benzoxazine ring structure.

Examples of monofunctional amines which function in forming benzoxazines include those with up to 40 carbon atoms such as ammonium; methylamine; ethylamine; propylamine; butylamine; isopropylamine; octadecylamine; cyclohexylamine; alkylamine; 1-aminoanthracene; 4-aminobenzaldehyde; 4-aminobenzophenone; aminobiphenyl; 2-amino-5-bromopyridine; 3-amino-ε-caprolactam; 2-amino-2,6-dimethylpiperidine; 3-amino-9-ethyl-carbazole; 4-(2-aminoethyl)morpholine; 2-aminofluorenone; 2-aminofluorene; 1-aminohomopiperidine; 9-aminophenanthrene; 1-aminopyrene; 4-bromoaniline; aniline; and others.

Suitable di-functional amines include those with up to 40 carbon atoms such as 2-aminobenzylamine; 1,3-diaminopropane; 1,4-diaminobutane; 1,10-diaminodecane; 2,7-diaminofluorene; 1,4-diaminocyclohexane; 9,10-diaminophenanthrene; 1,4-diaminopiperazine; 1,4-methylenedianiline; 1,4-diaminobenzophenone; 4,4'-diaminodiphenylsulfone; methylenedianiline; fluorenediamine; 4,4'-diaminodiphenylsulfide; 4,4'-oxydianiline; and others.

Suitable tri-functional amines include melamine, etc., while tetra-functional amines comprise fluorene-tetraamine; tetraaminediphenylether; and the like.

Other suitable amines include amine-terminated polydimethylsiloxane and copolymers thereof; amine-terminated polybutadiene and its copolymers; polyallylamine; and the like.

The following examples illustrate how functionalized benzoxazines can be prepared, polymerized and evaluated.

Stoichiometric amounts of solid bisphenol-A, paraformaldehyde, and liquid 3-aminophenylacetylene were mixed together at 100° C. for 15 minutes. A reaction temperature of 80° C. was found to be optimal for synthesis of a monofunctional benzoxazine based upon phenol. Bis(3-phenyl-3,4-dihydro-2H-1,3-benzoxazinyl) isopropane was synthesized by the general solvent method. The solvent method is discussed in papers such as X. Ning and H. Ishida, J. Polym. Sci., Chem. Ed., 32, 1121 (1994) The product was dissolved in chloroform and washed with a 3N solution of sodium hydroxide for purification. The solvent (if present) was evaporated with a rotary evaporation and the sample was dried overnight at 50° C. in a vacuum oven. The yield of the reaction was 80–85% in terms of benzoxazine ring content and the purity of the obtained benzoxazine monomer after purification was 97–99% as determined from proton nuclear magnetic resonance spectroscopy ('H NMR) and size exclusion chromatography (SEC). The purified benzoxazine samples were polymerized in a circulating air oven or in the chamber of a thermogravimetric analyzer under a nitrogen atmosphere.

EXAMPLE A (Ph-apa)

Benzoxazine from phenol (ph), formaldehyde and 3-aminophenylacetylene (apa) was prepared. Stoichiometric amounts of phenol, formaldehyde, and 3-aminophenylacetylene were reacted according to the general procedure given above at 80° C. It desirably has the structure:

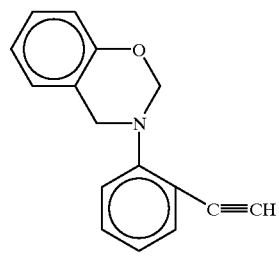

EXAMPLE B (Ph-apa)

Stoicheometric amounts of phenol, formaldehyde, and 4-(3-aminophenoxy)-4'-phenylethynylbenzophenone (apc) were reacted according to the general procedure. It desirably has the structure:

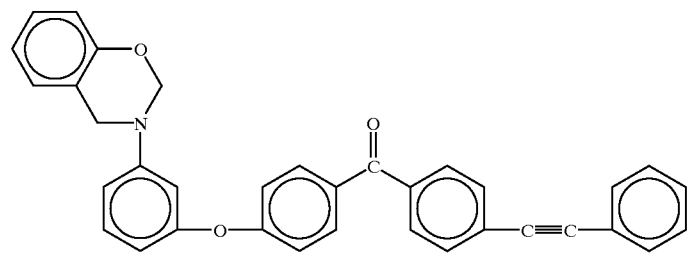

EXAMPLE C (BA-apa)

Stoichiometric amounts of 2,2-bis(4-hydroxyphenol)-propane (also known as bisphenol-A) (BA), formaldehyde and 3-aminophenylacetylene were reacted according to the general procedure. It desirably has the structure:

[Structure: bisphenol A-based bis-benzoxazine with 3-aminophenylacetylene groups]

EXAMPLE D (BS-apa)

Similar to Example C but

[Structure: HO–C6H4–SO2–C6H4–OH]

4,4'-dihydroxybenzosulfone (BS), was used instead of bisphenol A.

EXAMPLE E (BP-apa)

Similar to Example C but

[Structure: HO–C6H4–C6H4–OH (biphenyl diol)]

was used instead of bisphenol A.

EXAMPLE F (BAF-apa)

Similar to Example C but

[Structure: HO–C6H4–C(CF3)2–C6H4–OH]

was used instead of bisphenol A.

EXAMPLE G (NP-apa)

Similar to Example C but

[Structure: 2,7-dihydroxynaphthalene]

2,7-dihydroxynaphthalene was used instead of bisphenol A.

EXAMPLE H (BF-apa)

Similar to Example C but using bis(4-hydroxyphenol) methane was used instead of bisphenol A.

EXAMPLE I (BO-apa)

Similar to Example C but

[Structure: HO–C6H4–O–C6H4–OH]

was used instead of bisphenol A.

EXAMPLE J (BA-a) (control)

Stoichiometric amounts of bisphenol A, formaldehyde, and aniline were reacted according to the general procedure. Desirably the product had the structure:

[Structure: bisphenol A-based bis-benzoxazine with phenyl groups on N]

EXAMPLE K (HQ-apa)

Stoichiometric amounts of hydroquinone, formaldehyde and 3-aminophenylacetylene were reacted according to the general procedure.

Desirably the product had the structure:

[Structure: hydroquinone-based bis-benzoxazine with 3-aminophenylacetylene groups]

EXAMPLE L (BZ-apa)

Stoichiometric amounts of 4,4'-dihydroxybenzophenone, formaldehyde, and 3-aminophenylacetylene were reacted according to the general procedure.

The above samples were analyzed by FTIR to confirm that benzoxazine monomers were formed. Proton nuclear magnetic resonance spectra on a Varian Gemini-200 with a proton frequency of 200 MHz were also used to confirm analysis. Deuterated chloroform was used as solvent and tetramethylsilane (TMS) was used as an internal standard. Size exclusion chromatography using tetrahydrofuran as the solvent and a 254 nm U.V. detector was used to determine purity of the benzoxazines.

Thermal stability of the synthesized polybenzoxazines was investigated using a thermogravimetric analyzer with 1 μg sensitivity and an evolved gas analyser. Nitrogen or air were used as purge gases. Heating was 20° C./min. for all tests. Differential scanning calorimetry (DSC) was performed using a heating rate of 10° C./min., a nitrogen purge, and an empty aluminum pan as a reference. A hermetic pan was used for all DSC tests.

As is typical for acetylene functional polymers, the acetylene functional benzoxazines were yellow and turned dark brown or black during polymerization. According to literature acetylene can react under cationic, coordination, free radical, photolytic, and thermal inducement. Thermal polymerization of model diethynyl compounds in the literature showed reaction paths forming Strauss coupling, Diels-Alder products, trimers, tetramers, naphthalenes, and conjugated polyenes. One study of acetylene terminated imide reported 30% of the acetylenic groups underwent trimerization while the remainder was consumed by other reactions.

TABLE 1

Char Yields

| Example | Char wt. % in air 700° C. | Char in wt % $N_2$ 800° C. | Temp °C. at 5 wt. % loss air ($N_2$) | Temp °C. at 10 wt. % loss air ($N_2$) |
| --- | --- | --- | --- | --- |
| A (Ph-apa) | | 81 | (491) | (592) |
| B (Ph-apc) | | | | |
| C (BF-apa) | | 78 | (470) | (575) |
| D (BS-apa) | 28 | 79 | 378 (489) | 422 (592) |
| E (BP-apa) | 19 | 73 | 452 (464) | 494 (492) |
| F (BAF-apa) | 19 | 71 | 427 (494) | 454 (539) |
| G (NP-apa) | 30 | 76 | 377 (380) | 437 (428) |
| H (BF-apa) | | 74 | — (458) | — (524) |
| I (BO-apa) | | 75 | (415) | (513) |
| J (BA-a) (Cntrl) | | 32 | (390) | (425) |
| K (HQ-apa) | | 81 | (440) | (540) |
| L (BZ-apa) | | 80 | (478) | (547) |

Examples A–L above were polymerized prior to analysis in an air or nitrogen environment so the effect of the additional functional groups on thermal stability and char yields could be qualitatively observed. Example J was the only benzoxazine without additional functional groups. Example J yielded only 32 weight percent at 800° C. in nitrogen while all the functionalized benzoxazines yielded at least 70 weight percent char under identical conditions. This illustrates the dramatic increases in char yield that may be expected with this technology.

The benzoxazine monomers and oligomers are precursors to polybenzoxazines. The polymers are useful as rigid high temperature polymers and polymers for transportation vehicles, electrical circuitry etc. The polymers are also useful as precursor for high char yielding materials such as are used for aircraft brakes etc. Besides being stable to high temperatures the benzoxazines tend not to support combustion as much as other polymers. This is an important feature in minimizing the spreading of combustion in transportation vehicles (planes, rockets, cars, buses, etc.) as well as in electronic components (computers, electrical devices, communication or broadest equipment, etc.). Table II below illustrates the desirability of polybenzoxazines with additional functional groups in applications where flame barriers or low flammability are needed. The results are from microconecalorimetry which has been correlated with conecalorimetry by the Federal Aviation Administration in Atlantic City, New Jersey. A low total heat release is desirable as it indicates the material does little to propagate a flame. A low peak heat release is desirable as it indicates a low rate of energy input to a flame.

Desirably at least 25, 50, 75 or 90 mole percent of the amine component of said benzoxazine includes at least one of said functional group(s) and/or desirably at least 25, 50, 75, or 90 mole percent of the phenolic component includes at least one of said functional group(s).

TABLE II

Microconecalorimetry

| Sample | Peak Heat Release Watts/g | Total Heat Release kJ/g |
| --- | --- | --- |
| Nylon-6 | 680 | 19 |
| Polyphenylenesulfide | 400 | 12 |
| Polyetherimide | 180 | 10 |
| Polyetheretherketone PEEK | 50 | 7.5 |
| Polybenzoxazine (acetylene functionalized) | 30 | 2.5 |

Ortho, meta, and para substituted aminobenzonitrile were reacted into benzoxazines using phenol and formaldehyde. They had the chemical structures shown below.

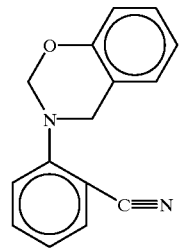

I(a)

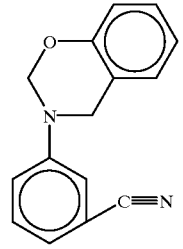

I(b)

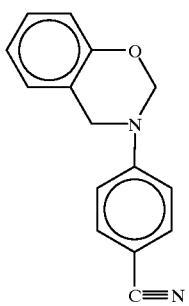

These were analyzed by FTIR and DSC due to an interest in the potential high thermal stability of ring structures from the cyclotrimerization of the phthalonitrile resins. Phthalonitrile resins cured with amines are known to result in high char yield eg>70 weight percent when postcured at 316° for 16 hours.

Benzoxazines were also prepared from 4-aminophthalonitrile. They had the formulas given below.

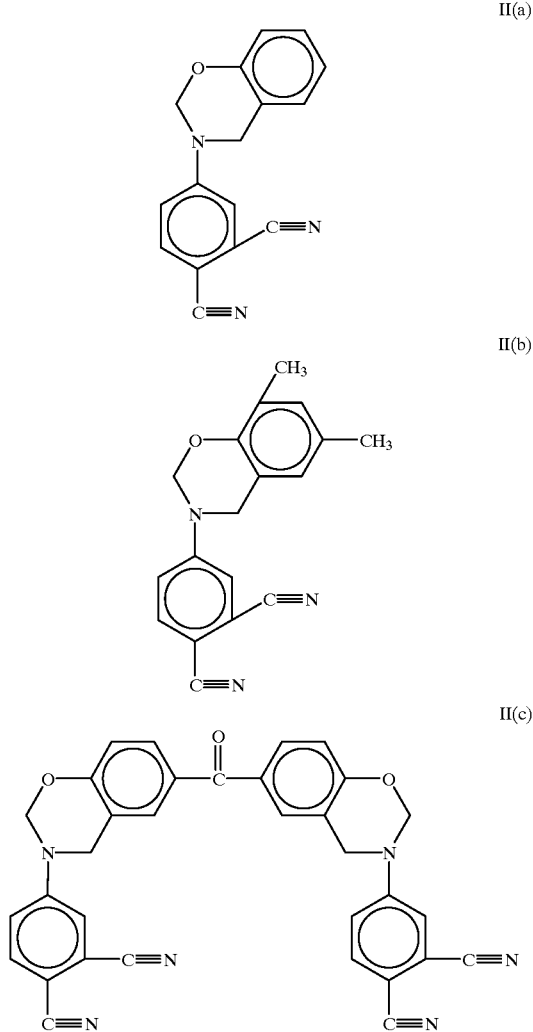

The 4-aminophthalonitrile had low reactivity in the reaction to form a benzoxazine. Therefore, the reaction was ran in a solvent method in acidic conditions. 4-Aminophthalonitrile was added dropwise into a solution of formaldehyde in dioxane. The mixture was stirred 30 minutes before adding a stoichiometric amount of phenol. The pH was controlled near 1 by adding a trace of hydrochloric acid in deionized water. The temperature was raised to 90° C. and the reaction mixture was refluxed for 6 hours. The as synthesized product was dissolved in chloroform and washed with a 3N solution of sodium hydroxide. The solvent was then evaporated by a rotary evaporation and the sample was dried in a vacuum oven overnight at 60° C. The yield was 70–75% in terms of benzoxazine compounds. The monomer was purified to 97–99% as determined by $^1$H-NMR. The side products appeared to be dimers. Most of the other benzoxazines were prepared by solventless methods at temperatures of about 125° C. for about 30–60 minutes to obtain 95% yield. The purified samples were polymerized isothermally in a nitrogen circulated oven at 220° C. unless otherwise specified. The char yield was determined as the weight of the remaining material as a percent of sample weight after heating to 800° C. under nitrogen purge at a heating rate of 20° C./min. The samples were polymerized benzoxazines.

The para substituted nitrile compound I(C) was heated to 350° C. and analyzed by FTIR. The results were interpreted to indicate that the para nitrile groups trimerized to form a triazine ring. The meta substituted nitrile compound I(b) was heated to 350° C. The FTIR data indicated that while the oxazine ring opening polymerization occurred in I(b) the trimerization of nitrile did not occur. Based on this limited data and FTIR analysis of compounds II(a), II(b) and 11(c) (which have both meta and para nitrile groups) it appears that para nitrile groups trimerize at lower temperatures than meta nitrile groups. Compound II(a) was heated to 250° C. for 4 hours after which complete oxazine ring opening polymerization was thought to have occurred. Only about a 50% decrease of the infrared peak for the nitrile group was observed after this time. The remainder of the peak can be eliminated by heating to a higher temperature such as 600° C.

The following Table III illustrates estimated temperatures where benzoxazine ring opening polymerization (Tcure (benzox)) and curing through a reaction of the pendant nitrile group (Tcure(nitrile)) occurred for the specific compounds synthesized. The estimated ΔH values are also given.

TABLE III

| Monomer | Tcure (benzox) [°C.] | Tcure (nitrile) [°C.] | ΔHbenzox [J/g] | ΔHnitrile [J/g] |
|---|---|---|---|---|
| Ia | 257 | 257 | 115 | — |
| Ib | 253 | — | — | — |
| Ic | 248 | 350 | 100 | — |
| IIa | 268 | 290 | 83 | 57 |
| IIb | 314 | 330 | 34 | 67 |
| IIIa | 253 | 285 | 21 | 100 |

Table III can be interpreted in the following manner. Compounds I(a), I(b), and I(c) showed about the same Tcure (benzox) regardless of whether the nitrile group was ortho, meta, or para. The Tcure (nitrile) was affected by the ortho, meta, para position of the nitrile group such that the ortho cured at the lowest temperature, then the para, and the meta may not have cured significantly in the temperature range tested. As previously mentioned a temperature of about 600° C. would be anticipated to cause curing or other reaction of the meta nitrile group.

Table III also shows that the methyl substituents on the phenol increased the Tcure (benzox) and the Tcure (nitrile). One optimizing extent of cure at low temperatures may want to minimize such substituents and/or other substituents in those locations.

Char yields of 77 weight percent and 80 weight percent were achieved starting with compounds II(a) and III(a) which are much higher than achieved with traditional benzoxazines. Char yields of 57–61 weight percent were achieved starting with compounds I(a), I(b) and I(c) which are higher than traditional benzoxazines.

While in accordance with the patent statutes the best mode and preferred embodiment has been set forth, the scope of the invention is not limited thereto, but rather by the scope of the attached claims.

What is claimed is:

1. A benzoxazine compound, comprising:

a benzoxazine containing molecule being the reaction product of at least one phenolic compound, at least one primary amine and at least one aldehyde, said reaction product including at least one pendant functional group sufficiently reactive with itself or other pendant functional groups in said reaction product at temperatures from about 25° C. to about 300° C. to form a chemical bond between two benzoxazine containing molecules of said reaction product, said phenolic compound including one or more phenolic groups having the formula

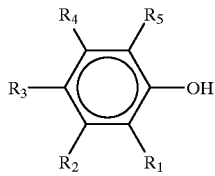

wherein $R_1$ through $R_5$ independently is OH; H; a linear or branched aliphatic having from 1 to 10 carbon atoms; a methylene group, isopropylidene group, an oxygen atom, a carbonyl group, a sulfonyl group, a hexafluoroisopropylidene group an aromatic having from 6 to 12 carbon atoms; a combination of an aliphatic and an aromatic having from 7 to 12 carbon atoms; a phosphorus containing group compound having from 0 to 6 carbon atoms, an amine containing group having from 0 to 6 carbon atoms; or a halogen, wherein at least one of $R_1$ or $R_5$ ortho to said OH group must be a hydrogen, and optionally wherein a non-hydrogen and non-halogen $R_1$ through $R_5$ group can serve to connect two or more phenolic groups.

2. A benzoxazine compound according to claim 1, wherein said pendant functional group comprises

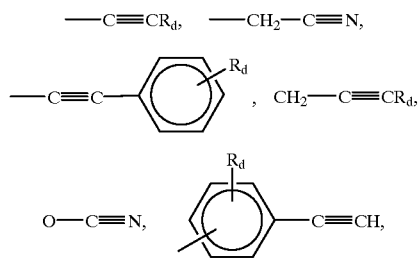

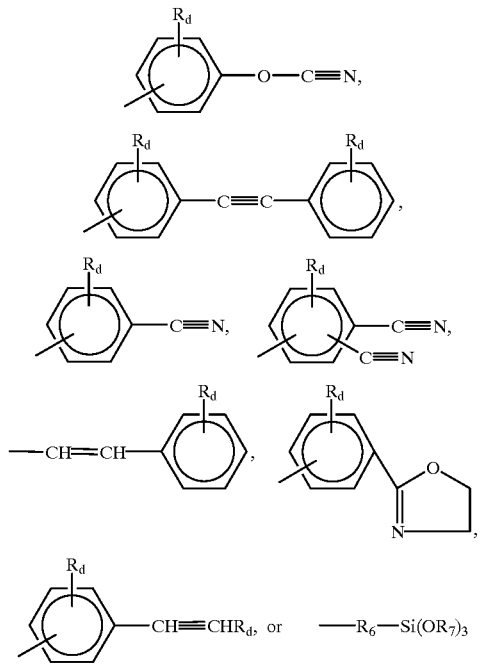

or combinations of said functional groups wherein $R_6$ is an alkylene group of 1 to 10 carbon atoms or an aromatic group of 6 to 12 carbon atoms or combinations thereof, $R_7$ is an alkyl of 1 to 5 carbon atoms, phenyl or chlorine, and $R_d$ is one or more H, halogen, alkyl of 1 to 6 carbon atoms, or an aromatic, alkyl substituted aromatic, or aromatic substituted alkyl group of 6 to 12 carbon atoms.

3. A benzoxazine compound according to claim 1, wherein said at least one pendant functional group comprises a) at least one first pendant

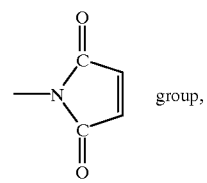

group, and at least one second pendant

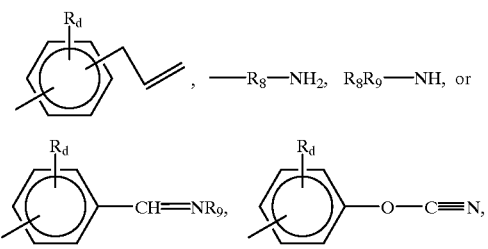

-continued

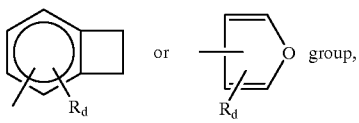

or combinations thereof wherein $R_8$ is selected from alkylenes of 1 to 6 carbon atoms; aromatic, aromatic substituted alkylene, and alkyl substituted aromatic groups of 6 to 12 carbon atoms and $R_9$ is independently selected from alkyl groups of 1 to 6 carbon atoms; aromatic, aromatic substituted alkyl or alkyl substituted aromatic groups of 6 to 12 carbon atoms or b) at least one first pendant

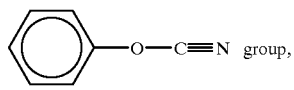

and at least one second pendant

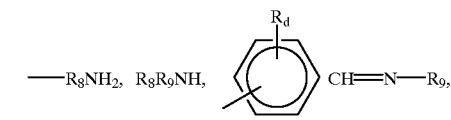

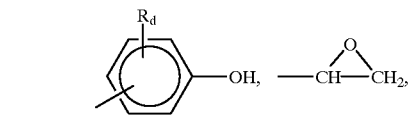

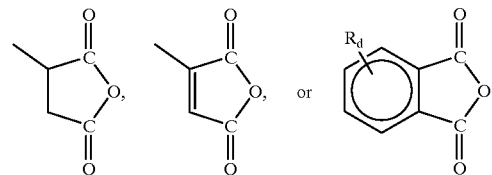

group, wherein $R_8$ and $R_9$ are as previously described or combinations of said first and second pendant groups, or c) at least one first pendant

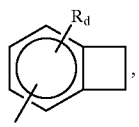

and at least one second pendant

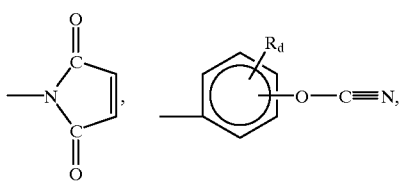

pr —C≡C—$R_d$ group, or combinations thereof, or d) at least one first pendant

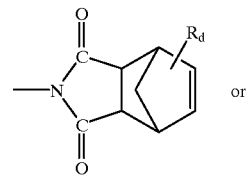

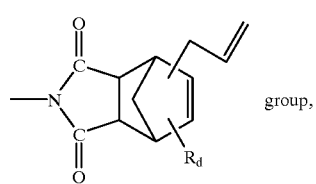

and at least one second pendant

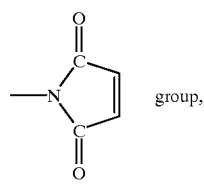

e) at least one first pendant

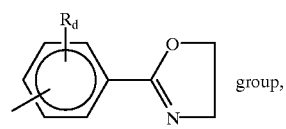

and at least one second pendant

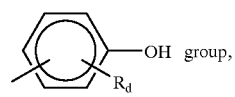

group, or f) at least one first pendant SiH group, and at least one second pendant —CH=CHR$_d$ group, or g) at least one first

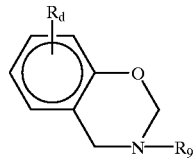

and at least one second

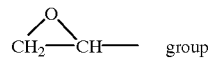

wherein $R_d$ is one or more pendant H; halogen; alkyl group of 1 to 6 carbon atoms; or aromatic, alkyl substituted aromatic, or aromatic substituted alkyl group of 6 to 12 carbon atoms.

4. A benzoxazine compound according to claim 1, wherein said primary amine includes said functional group and said phenolic compound comprises

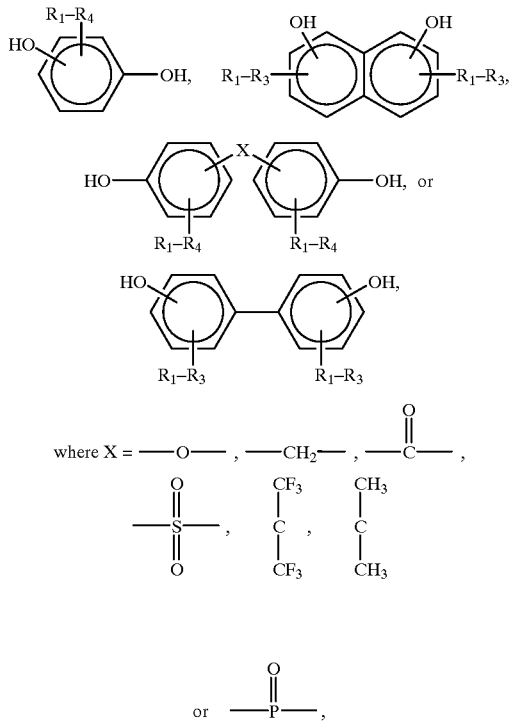

and where $R_1$ through $R_5$ are defined as in claim 1.

5. A benzoxazine compound according to claim 2, wherein said primary amine includes pendant functional group and said phenolic compound comprises

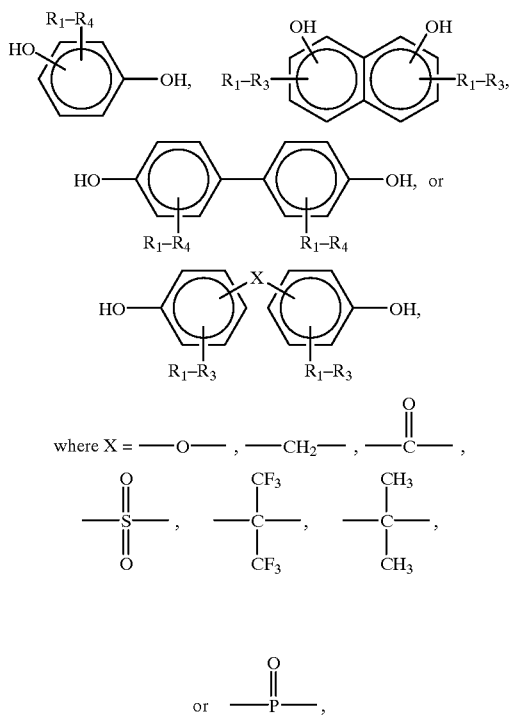

and where $R_1$ through $R_5$ are defined as in claim 1.

6. A benzoxazine compound according to claim 3, wherein said primary amine includes said pendant functional group and said phenolic compound comprises

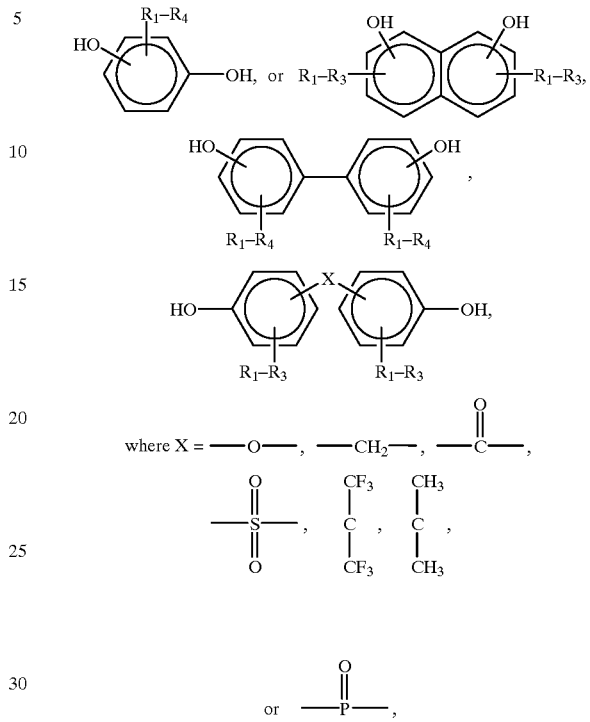

and where $R_1$ through $R_5$ are defined as in claim 1.

7. A polybenzoxazine comprising the ring opening polymerization reaction product of a benzoxazine containing molecule being the reaction product of at least one phenolic compound, at least one primary amine and at least one aldehyde, said reaction product including at least one pendant functional group sufficiently reactive with itself or other pendant functional groups in said reaction product at temperatures from about 25° C. to about 300° C. to form a chemical bond between two benzoxazine containing molecules of said reaction product, said phenolic compound including one or more phenolic groups having the formula

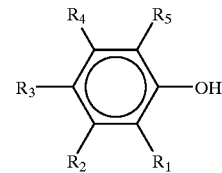

wherein $R_1$ through $R_5$ independently is OH; H; a linear or branched aliphatic having from 1 to 10 carbon atoms; a methylene group, isopropylidene group, an oxygen atom, a carbonyl group, a sulfonyl group, a hexafluoroisopropylidene group, an aromatic having from 6 to 12 carbon atoms; a combination of an aliphatic and an aromatic having from 7 to 12 carbon atoms, a phosphorus containing group having from 0 to 6 carbon atoms, an amine containing group having from 0 to 6 carbon atoms; or a halogen, wherein at least one of $R_1$ or $R_5$ ortho to said OH group must be a hydrogen, and optionally wherein a non-hydrogen and non-halogen $R_1$ through $R_5$ group can serve to connect two or more phenolic groups.

* * * * *